(12) United States Patent
Sudo et al.

(10) Patent No.: US 8,716,523 B2
(45) Date of Patent: *May 6, 2014

(54) CATALYST FOR USE IN PRODUCTION OF METHACRYLIC ACID AND METHOD FOR MANUFACTURING THE SAME

(75) Inventors: Atsushi Sudo, Takasaki (JP); Tatsuhiko Kurakami, Sanyoonoda (JP); Toshitake Kojima, Takasaki (JP); Shigeo Hayashimoto, Kita-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 1090 days.

This patent is subject to a terminal disclaimer.

(21) Appl. No.: 11/887,017

(22) PCT Filed: Mar. 28, 2006

(86) PCT No.: PCT/JP2006/306318
§ 371 (c)(1),
(2), (4) Date: Nov. 8, 2007

(87) PCT Pub. No.: WO2006/104155
PCT Pub. Date: Oct. 5, 2006

(65) Prior Publication Data
US 2009/0234158 A1 Sep. 17, 2009

(30) Foreign Application Priority Data
Mar. 29, 2005 (JP) .................. 2005-094734

(51) Int. Cl.
*C07C 51/235* (2006.01)
*B01J 23/22* (2006.01)
(52) U.S. Cl.
USPC .......................... 562/535; 502/312
(58) Field of Classification Search
CPC ............................ C07C 51/252; B01J 27/198
See application file for complete search history.

(56) References Cited

U.S. PATENT DOCUMENTS

| | | | | |
|---|---|---|---|---|
| 4,225,466 | A | * | 9/1980 | Wada et al. ............. 502/209 |
| 4,259,211 | A | * | 3/1981 | Krabetz et al. ............ 502/178 |
| 5,198,579 | A | * | 3/1993 | Honda et al. .............. 562/535 |
| 5,716,895 | A | * | 2/1998 | Sugi et al. ............... 502/24 |
| 6,812,188 | B2 | | 11/2004 | Seo et al. |
| 7,825,061 | B2 | | 11/2010 | Sudo et al. |
| 8,017,547 | B2 | | 9/2011 | Sudo et al. |
| 8,148,291 | B2 | | 4/2012 | Sudo et al. |
| 2002/0052529 | A1 | | 5/2002 | Kase et al. |
| 2007/0010394 | A1 | | 1/2007 | Atsushi et al. |
| 2011/0237829 | A1 | | 9/2011 | Sudo et al. |

FOREIGN PATENT DOCUMENTS

| | | |
|---|---|---|
| CN | 1461236 A | 12/2003 |
| DE | 19922156 A1 | 8/2000 |
| EP | 1 325 780 | 7/2003 |
| EP | 1 595 600 A1 | 11/2005 |
| JP | 57-165040 A | 10/1982 |
| JP | 4-63139 A | 2/1992 |
| JP | 8-157414 | 6/1996 |
| JP | 9-75740 | 3/1997 |
| JP | 9-290162 A | 11/1997 |
| JP | 9-299803 | 11/1997 |
| JP | 2003-10691 | 1/2003 |
| JP | 2004-188231 | 7/2004 |
| JP | 2005-21727 | 1/2005 |
| JP | 2005-58909 | 3/2005 |
| JP | 2005-131577 | 5/2005 |
| JP | 2005-187463 | 7/2005 |
| JP | 2005-272313 | 10/2005 |
| WO | 2004/073857 A1 | 9/2004 |

OTHER PUBLICATIONS

The Singapore communication dated Dec. 3, 2009.
The International Search Report dated Apr. 25, 2006.
The European communication dated Jul. 31, 2009.
Chinese communication dated Sep. 25, 2009.
International Search Report dated Jul. 4, 2006 in co-pending U.S. Appl. No. 11/919,911.
Singapore Communication dated May 27, 2009, in co-pending U.S. Appl. No. 11/919,911.
Chinese Communication dated Jun. 23, 2009 with English translation in co-pending U.S. Appl. No. 11/919,911.
Chinese Communication dated Feb. 5, 2010 with English translation in co-pending U.S. Appl. No. 11/919,911.
Chinese Communication dated Aug. 4, 2010 in co-pending U.S. Appl. No. 11/919,911, corresponding Foreign Application CN200680016315.9.
Singapore Communication dated Nov. 9, 2010 in corresponding Singapore Application No. 200708866-9 U.S. Appl. No. 11/887,017.
European communication dated May 28, 2010 in co-pending foreign application (06730266.1).
European communication dated May 28, 2010 in co-pending foreign application (10156028.2).
Korean Communication, with English translation, dated May 3, 2012 in corresponding Korean Patent Application No. 10-2012-7009218.
Office Action dated Sep. 2, 2011 in co-pending U.S. Appl. No. 13/155,863.
Chinese Communication, with English translation, dated Sep. 13, 2012 in corresponding Chinese patent application No. 201010143947X.
Notice of Allowance mailed Dec. 15, 2011 in co-pending U.S. Appl. No. 13/155,863.
Miscellaneous Communication mailed Jan. 1, 2012 in co-pending U.S. Appl. No. 13/155,863.

(Continued)

*Primary Examiner* — Paul A Zucker
(74) *Attorney, Agent, or Firm* — Nields, Lemack & Frame, LLC

(57) ABSTRACT

A method for manufacturing a catalyst of which active components are partly neutralized salt of heteropoly acid comprising molybdenum, phosphorus, vanadium, cesium, antimony, and ammonia as essential components, wherein the method is characterized in mixing an antimony compound with a complex oxide of the essential active components in the catalyst containing active components other than antimony, wherein the antimony compound may be added during slurry preparation.

13 Claims, No Drawings

(56) References Cited

OTHER PUBLICATIONS

Indian Communication dated Feb. 1, 2013 in corresponding Indian patent application No. 4838/CHENP/2007.
Office Action dated Jul. 19, 2011 in co-pending U.S. Appl. No. 13/155,863.
European Communication dated Oct. 7, 2011 in corresponding European Patent Application No. EP 06730266.1.
Indonesian Communication, with English translation, dated Feb. 17, 2011 in co-pending foreign patent application No. W-00 2007 03746.
Office Action Feb. 25, 2011 in co-pending U.S. Appl. No. 11/919,911.
Korean Communication, with English translation, dated Feb. 22, 2012 in corresponding Korean patent application No. KR 10-2007-7021745.
Taiwanese Communication, with English translation, dated Mar. 29, 2012 in corresponding Taiwan Patent Application No. 095110953.
Notice of Allowance dated Jun. 9, 2011 in co-pending U.S. Appl. No. 11/919,911.
Chinese Communication, with English translation, dated Jan. 26, 2011 in corresponding foreign application No. CN 201010143947X.
Japanese Communication, with English translation, mailed Sep. 30, 2010 in corresponding Japanese patent application No. 2005-094734.

* cited by examiner

CATALYST FOR USE IN PRODUCTION OF METHACRYLIC ACID AND METHOD FOR MANUFACTURING THE SAME

FIELD OF THE INVENTION

The present invention relates to a catalyst for use in the production of methacrylic acid by gas-phase catalytic oxidation of methacrolein, isobutyraldehyde, or isobutyric acid using a highly active and highly selective catalyst and a method for manufacturing the catalyst.

BACKGROUND OF THE PRESENT INVENTION

Background Art

Many catalysts have been proposed for use in the production of methacrylic acid by the gas-phase catalytic oxidation of methacrolein, isobutyraldehyde, or isobutyric acid. Most of these catalysts contain molybdenum and phosphorus as the main components and have a structure of heteropolyacid and/or salt thereof.

For example, Patent Document 1 describes in detail the roles of individual elements in a catalyst containing molybdenum, vanadium, phosphorus, and arsenic as essential components and a method for preparing the catalyst. Patent Document 2 describes in detail the roles of individual elements in a catalyst containing molybdenum, phosphorus, vanadium, antimony, and copper as essential components and a method for preparing the catalyst. Patent Document 2 describes that a catalyst containing vanadium and antimony prepared by a specific method has a high reactivity, a high methacrylic acid selectivity, and long catalyst life. Patent Document 3 describes the preparation of a molybdenum, phosphorus, vanadium, antimony, and copper-based catalyst. In this preparation, catalyst raw materials other than a vanadium raw material and/or an antimony raw material are dissolved or suspended in water, heat-treated at a temperature of 80° C. to 200° C. for 1 to 24 hours in the presence of an ammonium group, followed by the addition of a vanadium raw material and/or an antimony raw material, heat-treated again at a temperature of 80° C. to 200° C. for 1 to 24 hours, and calcined.

Patent Document 4 describes the preparation of a molybdenum, phosphorus, vanadium, antimony, and copper-based catalyst. In the preparation, an antimony component is pre-mixed with a molybdenum component, a vanadium component and/or a copper component. The mixture is heat-treated at 400° C. to 800° C. and is used in a catalyst raw material.

In these known techniques, the addition of an antimony compound is designed to increase the activity of the resulting catalyst. However, the addition of an antimony compound is complicated or time-consuming. Thus, there is a demand to establish a simple manufacturing method.

Furthermore, these catalysts have lower activity, lower selectivity to a target substance, and shorter life than a molybdenum-vanadium-based catalyst proposed in the production of acrylic acid by the oxidation of acrolein, which is known to be similar to the gas-phase catalytic oxidation reaction of methacrolein, isobutyraldehyde, or isobutyric acid. Thus, although some of these catalysts have been commercialized, there is a demand for improved performance of catalyst.

The optimum activity (conversion of raw materials) of a catalyst depends on reaction conditions (space velocity, molar ratio of raw material gases, diameter of a reaction tube, and the like). Excessively high catalyst activity proceeds a successive oxidation reaction, leading to a lower yield of methacrylic acid. Excessively low catalyst activity results in an increase in the temperature of a reaction bath. Thus, the catalyst cannot resist a long period of use. Thus, a method for controlling the catalyst activity is also required to be adapted to various reaction conditions.

Patent Document 5 describes a method for filling a plurality of reaction zones provided by longitudinally dividing a reactor with a plurality of catalysts having different activities such that the activities of the catalysts increase from the inlet to the outlet of a raw material gas. This can reduce heat generation in the reactor to some extent. However, the filling process is troublesome. In an example and a comparative example of Patent Document 5, while a reaction is performed with two types of catalysts having an activity controlled by adjusting the antimony level, when these catalysts are used in monolayer, the catalyst of a lower antimony level has a very low activity and the catalyst of a higher antimony level has a high activity but a low selectivity. Both of the catalysts exhibit low yields. In addition, even a catalyst having an intermediate composition of the two catalysts exhibits a low yield and a high $\Delta T$ (hot spot temperature—heat medium bath temperature). This may cause deterioration due to heat load.

[Patent Document 1] Japanese Patent No. 3146486
[Patent Document 2] Japanese Unexamined Patent Application Publication No. 9-24277
[Patent Document 3] Japanese Patent No. 3482476
[Patent Document 4] Japanese Unexamined Patent Application Publication No. 6-91172
[Patent Document 5] Japanese Patent No. 2574948

SUMMARY OF THE INVENTION

It is an object of the present invention to provide a simple method for manufacturing a catalyst for use in gas-phase catalytic oxidation of methacrolein, isobutyraldehyde, or isobutyric acid to produce methacrylic acid selectively and consistently in a high yield for a long period of time and a method for simply controlling the catalyst activity to be adapted to various reaction conditions.

The present inventors found that in a partially neutralized heteropolyacid salt containing essential components of molybdenum, phosphorus, vanadium, cesium, antimony, and ammonia, a catalyst containing an antimony compound added by a particular method has a very high catalytic performance. The present inventors also found that the catalyst activity can be simply and precisely controlled by the addition of antimony by a particular method. The present inventors further found that antimony has an effect opposite to that in Patent Document 5. Thus, the present inventors completed the present invention.

Thus, the present invention relates to (1) a method for manufacturing a catalyst comprising essential active components of molybdenum, phosphorus, vanadium, cesium, antimony, and ammonia for use in the production of methacrylic acid, comprising mixing an antimony compound with a complex oxide containing the essential active components other than antimony, and molding and calcining the resulting mixture, (2) the method according to (1), wherein the mixing of the antimony compound with the complex oxide is a mechanical mixing of the complex oxide and a solid antimony compound, (3) a method for manufacturing a catalyst comprising essential active components of molybdenum, phosphorus, vanadium, cesium, antimony, and ammonia for use in the production of methacrylic acid, comprising mixing a slurry containing the essential active components other than antimony and being convertible into a complex oxide by heating with an antimony compound, drying the resulting mixture to form a dry powder, and molding and calcining the dry powder.

(4) the method according to (3), wherein the temperature at which the antimony compound is mixed is 0° C. to 35° C.,
(5) the method according to (1) or (2), wherein the molding comprises coating an inactive carrier with the mixture using a binder to form a coated catalyst,
(6) the method according to (3) or (4), wherein the molding comprises coating an inactive carrier with the dry powder using a binder to form a coated catalyst,
(7) the method according to (5) or (6), wherein the binder is water and/or at least one type of liquid selected from the group consisting of an organic compound having a boiling point of 150° C. or less at 1 atmospheric pressure,
(8) the method according to any one of (1) to (7), wherein the calcination temperature is 300° C. to 450° C.
(9) a catalyst prepared by the method according to any one of (1) to (8), and
(10) a method for producing methacrylic acid, comprising gas-phase catalytic oxidation of methacrolein, isobutyraldehyde, or isobutyric acid using a catalyst according to (9).

Advantages Effect of the Invention

According to the present invention, a highly active and highly selective catalyst containing essential components of molybdenum, phosphorus, vanadium, cesium, antimony, and ammonia can be manufactured, a catalyst of which activity can easily be controlled and which can be adapted to various reaction conditions can be provided.

DESCRIPTION OF THE PREFERRED EMBODIMENTS

A manufacturing method according to the present invention includes mixing an antimony compound with an aqueous solution containing a compound containing active components (molybdenum, phosphorus, vanadium, cesium, and ammonia) of a catalyst or a water dispersion of the compound (hereinafter collectively referred to as slurry) or a complex oxide formed by drying the slurry.

Preferred embodiments of a manufacturing method according to the present invention are roughly divided into the following two types depending on the form of the complex oxide or the slurry (collectively referred to as precursor A).
(1) Compounds each containing one or more of molybdenum, phosphorus, vanadium, cesium, ammonia, and other optional element are dissolved and/or dispersed in water (step (a)) to prepare a slurry. The slurry is dried (step (b)) to prepare a precursor A. The precursor A and an antimony compound powder are mixed (step (c)), then molded (step (d)), and calcined (step (e)).
(2) Compounds each containing one or more of molybdenum, phosphorus, vanadium, cesium, ammonia, and other optional element dissolved and/or dispersed in water (step (f)) to prepare a slurry. The slurry is mixed with an antimony compound (step (g)), dried (step (h)), molded (step (i)), and calcined (step (j)).

In the present invention, an active component other than molybdenum, phosphorus, vanadium, cesium, antimony, and ammonia may be at least one element selected from the group consisting of copper, arsenic, silver, manganese, zinc, aluminum, boron, germanium, tin, lead, titanium, zirconium, chromium, rhenium, bismuth, tungsten, iron, cobalt, nickel, cerium, thorium, potassium, and rubidium. A component other than the essential components may be added by any method, provided that a uniform complex oxide powder or slurry can be obtained. The component other than the essential components may be added before or after the addition of an antimony compound.

In the present invention, the atomic ratio of a compound containing an active component to 10 molybdenum atoms is generally 0.1 to 6, preferably 0.3 to 2.0 for vanadium, generally 0.5 to 6, preferably 0.7 to 2.0 for phosphorus, generally 0.01 to 4.0, preferably 0.1 to 2.0 for cesium, generally 0.1 to 10.0, preferably 0.5 to 5.0 for ammonium, and generally 0.01 to 5, preferably 0.05 to 2.0 for antimony. The type and the amount of another optional active component are determined as appropriate to provide a catalyst having optimum performance depending on the condition under which the catalyst is used. The atomic ratio of a catalyst active component in the present invention is that in the preparation of raw materials and does not contain oxygen.

An embodiment will be described below for the processes described above.

Step (a) and (f): Preparation of Slurry

In the present invention, examples of a compound containing an active component for use in the preparation of a catalyst include a chloride, a sulfate, a nitrate, an oxide, or an acetate of an active component element. Specifically, preferred examples of a compound containing an active component include a nitrate, such as potassium nitrate or cobalt nitrate, an oxide, such as molybdenum oxide, vanadium pentoxide, antimony trioxide, cerium oxide, zinc oxide, or germanium oxide, and an acid, such as orthophosphoric acid, phosphoric acid, boric acid, aluminum phosphate, or 12 tungstophosphoric acid (or salt thereof). Preferably, a cesium compound is cesium acetate or cesium hydroxide and a weak acid salt of cesium. Preferably, an ammonium compound is ammonium acetate or ammonium hydroxide. Compounds containing these active components may be used alone or in combination. A slurry can be formed by uniformly mixing each compound containing an active component and water. Preferably, in the preparation of the slurry, a compound containing molybdenum, vanadium, phosphorus, and an another optional metallic element is sufficiently dissolved before the addition of a cesium compound and an ammonium compound to the slurry. When a slurry is selected as the precursor A, the addition of essential active components other than an antimony compound is preferably followed by the addition of the antimony compound. Examples of an antimony compound include antimony trioxide, antimony pentoxide, and antimony acetate. Antimony trioxide is particularly preferred. As a metal compound other than essential active components in this case, use of a copper compound, such as copper acetate (cuprous acetate, cupric acetate, basic copper acetate, or cupric oxide, preferably cupric acetate) or copper oxide (cuprous oxide or cupric oxide) may have a preferred effect.

In the preparation of a slurry, the slurry is preferably heated to a temperature at which a compound containing molybdenum, phosphorus, vanadium, and another optional metallic element can be dissolved sufficiently. The temperature at which a cesium compound and an ammonium compound are added is generally 0° C. to 35° C., preferably about 10° C. to about 30° C. This tends to provide a catalyst having a higher activity. The amount of water in the slurry is not limited, provided that the whole quantity of compounds used in the slurry can completely be dissolved or uniformly be mixed, and is determined as appropriate in consideration of a drying method or drying conditions. In general, the amount of water in the slurry is about 200 to 2000 mass parts per 100 mass parts of the total compounds used in the preparation of the slurry. While a larger amount of water may be used, an excessive amount of water causes many demerits, such as an increase in the energy cost of a drying process and insufficient drying of the slurry.

Step (b) and (h): Drying

Then, the slurry formed in the step described above or in the following step (g) is dried to produce a dry powder (complex oxide). The slurry may be dried by any method, provided that the slurry is completely dried. Examples of a drying method include drum drying, freeze-drying, spray drying, and evaporation to dryness. Among them, the spray drying is particularly preferred in the present invention, because it can dry the slurry to form a powder or granules in a short time.

The temperature of the spray drying depends on the slurry concentration and the feed rate and is generally 70° C. to 150° C. at the outlet of a dryer. Preferably, a dry product has an average particle diameter of 30 to 700 μm.

Step (C): Mixing of Complex Oxide and Antimony Compound

A complex oxide and an antimony compound may be mixed by any method, provided that they are uniformly mixed. The complex oxide and/or the antimony compound may be mixed with water (c-1), or a solid complex oxide and a solid antimony compound are mixed mechanically (c-2). (c-2) is preferred because it is simple. When (c-1) is selected, the slurry is dried as in the step (b)

Step (G): Mixing of Slurry and Antimony Compound

The temperature at which a slurry and an antimony compound are mixed is not limited to a specific temperature and is preferably 0° C. to 35° C. Mixing of an antimony compound with a slurry before the addition of a cesium compound and an ammonium compound, in particular having a temperature of 35° C. or more, may result in a less active catalyst and is therefore not preferred.

Step (d), (i): Molding

To reduce pressure loss of reactant gas in oxidation reactions, the mixture obtained in the step (c) or the dry powder obtained in the step (h) are used after they are molded into columnar matters, tablets, ring shapes and spherical shapes and the like. Among these, coating inert carriers with them to provide coated catalysts is particularly preferred, because improvement in selectivity and removal of reaction heat are expected to be achieved.

Preferable coating step (step (d), (i)) is a tumbling granulation method as described below. This is a method to coat carriers with a coating mixture by, for example, rapidly rotating a flat or uneven disc in an apparatus having the disc at the inner bottom of a fixed container so as to stir carriers in the apparatus vigorously through their repetitive rotatory motion and orbital motion and by adding binders and the coating mixture comprising the mixture or dry powders and other optional additives, e.g., molding aiding agents and strength enhancing materials. Any of the following methods can be employed to add binders: 1) to premix the binders in the coating mixture, 2) to add the binders at the same time when the coating mixture is added into the fixed container, 3) to add the binders after the coating mixture is added into the fixed container, 4) to add the binders before the coating mixture is added into the fixed container, and 5) to divide the coating mixture and binders into separate portions and add the whole amount by combining the above 2-4) as appropriate. In the case of 5), it is preferable to control addition rate using auto feeders and the like to ensure that a defined amount is carried on the carriers without, for example, adhesion of the coating mixture to the wall of the fixed container and aggregation between the coating mixture.

Binders have no limitation so long as they are at least one type selected from a group consisting of water and organic compounds having boiling point no more than 150° C. at one atm. A specific example of the binders other than water includes alcohols such as methanol, ethanol, propanols, butanols, preferably alcohols having 1-4 carbons, ethers such as ethyl ether, butyl ether or dioxane, esters such as ethyl acetate or butyl acetate, ketones such as acetone or methyl ethyl ketone and aqueous solutions thereof, with ethanol being particularly preferred. When ethanol is used as a binder, it is preferable to make the ethanol/water ratio being 10/1-0/10 (mass ratio), more preferably 9/1-1/9 (mass ratio) by mixing with water. The amount of these binders used is usually 2-60 mass part, preferably 10-50 mass part to 100 mass part of the coating mixture.

A specific example of carriers that can be used in this invention include spherical carriers etc. of silicon carbide, alumina, silica-alumina, mullite and alundum and the like, which have a diameter of 1-15 mm, preferably 2.5-10 mm. The carriers used usually have pore ratio of 10-70%. Ratio between the carriers and the coating mixture used is usually in such an amount of coating mixture/(coating mixture+carriers)=10-75% by mass, preferably 15-60% by mass.

When the coating mixture is dominant, reactivity of coated catalysts tends to increase and their mechanical strength tends to decrease. In contrast, when the coating mixture is outnumbered, mechanical strength of coated catalysts tends to increase (i.e., smaller abrasive wear) and their reactivity tends to decrease.

The optionally used molding aiding agents as described above include silica gel, diatomaceous earth, alumina powder and the like. The amount of the molding aiding agents used are usually 1-60 mass part to 100 mass part of the mixture or dry powder.

It is also useful to optionally use inorganic fibers inert to active agents in the catalysts and reactive gases such as ceramic fibers and whisker etc, as strength enhancing materials for enhancing mechanical strength of catalysts. However, fibers reactive with catalytic components are not preferred, such as potassium titanate whisker and basic magnesium carbonate whisker. The amount of the fibers used is usually 1-30 mass part to 100 mass part of the mixture or dry powder.

The mixture or dry powders are coated to the carriers in this way, and the resulting coated products are usually approximately 3-15 mm in diameter.

Step (e), (j): Calcination

While coated catalysts obtained as described above may be used for gas-phase catalytic oxidation reactions as catalysts without further modification, calcination may sometimes preferably increase catalytic activity. In this case, calcination temperature is usually 100-450° C., preferably 250-420° C. and calcination time is 1-20 hours.

Calcination is usually conducted under air atmosphere, but it may be conducted under inert gas atmosphere such as nitrogen atmosphere or reducing gas atmosphere such as ethanol atmosphere. Calcination under inert gas atmosphere or reducing gas atmosphere may optionally be followed by calcination under air atmosphere.

Catalysts obtained as described above (hereinafter referred to as catalysts according to the invention) will be used to produce methacrylic acid by gas-phase catalytic oxidation of methacrolein, isobutyraldehyde or isobutyric acid.

In the following description, gas-phase catalytic oxidation reaction will be illustrated in which methacrolein, the most preferable material for use with the catalysts of the invention, is used.

Molecular oxygen or molecular oxygen containing gas is used in the gas-phase catalytic oxidation reaction. Ratio of molecular oxygen used to methacrolein is preferably in a range of 0.5-20 molar ratio, and particularly preferably in a range of 1-10 molar ratio. It is preferable to add water into raw material gas in a molar ratio of 1-20 to methacrolein in order to promote the reaction smoothly.

In addition to oxygen and optionally added water (usually included as water vapor), the raw material gas may contain gases inert to the reaction such as nitrogen, carbon dioxide and saturated hydrocarbon and the like.

Alternatively, methacrolein may be supplied as a gas obtained from oxidation of isobutylene, tert-butanol and methyl tert-butyl ether.

Reaction temperature of the gas-phase catalytic oxidation reaction is usually 200-400° C., preferably 260-360° C. and the amount supplied of the raw material gas expressed in space velocity (SV) is usually 100-6000 $hr^{-1}$, preferably 300-3000 $hr^{-1}$.

The gas-phase catalytic oxidation reaction can be conducted under either increased pressure or reduced pressure, however, pressure around atmospheric pressure is generally suitable.

EXAMPLE

The present invention will now be described more specifically by way of the examples, however, the invention is not limited to the examples.

Conversion rate, selectivity and yield are defined as follows.

Conversion rate=mole number of methacrolein reacted/mole number of methacrolein supplied×100

Selectivity=mole number of methacrylic acid produced/mole number of methacrolein reacted×100

Yield=mole number of methacrylic acid produced/mole number of methacrolein supplied×100

Example 1

1) Preparation of Catalyst

To 5680 ml of pure water were added 800 g of molybdic anhydride, 40.43 g of vanadium pentoxide and 73.67 g of 85% by mass orthophosphoric acid, stirred for three hours at 92° C. to yield rust-colored clear solution. The solution was then cooled to 15-20° C. and 458.2 g of an aqueous solution containing 9.1% by mass of cesium hydroxide and 629.1 g of an aqueous solution containing 14.3% by mass of ammonium acetate were gradually added at the same time, and maturation for one hour at 15-20° C. provided yellow slurry.

To the slurry, 709.9 g of an aqueous solution containing 6.3% by mass cupric acetate was gradually added, and additional maturation was performed for 30 minutes at 15-20° C.

The slurry was then spray dried to provide complex oxide. The composition of the complex oxide produced is $Mo_{10}V_{0.8}P_{1.15}Cu_{0.4}Cs_{0.5}(NH_4)_{2.1}$.

320 g of the complex oxide, 6.9 g of antimony trioxide and 45 g of strength enhancing material (ceramic fiber) were uniformly mixed and coat molded to 300 g of spherical porous alumina carriers (particle diameter 3.5 mm) using approximately 80 g of 90% by mass ethanol aqueous solution as a binder. Resultant molding was calcined for five hours at 380° C. under flowing air to give a desired coated catalyst (catalyst according to the invention).

Active component composition of the catalyst obtained was $Mo_{10}V_{0.8}P_{1.15}Cu_{0.4}Cs_{0.5}(NH_4)_{2.1}Sb_{0.3}$.

2) Catalytic Oxidation Reaction of Methacrolein 10.3 mL of the coated catalyst obtained was filled in a stainless steel reaction tube with inner diameter of 18.4 mm, methacrolein oxidation reaction was performed using a condition of raw material gas (composition (mole ratio); methacrolein:oxygen:water vapor:nitrogen=1:2:4:18.6), space velocity (SV) 1200 $hr^{-1}$ and reaction bath temperature 310° C. The reaction was initially continued for three hours at reaction bath temperature of ~310° C., then reaction bath temperature was raised to 350° C. and the reaction was continued for 15 hours (this treatment is hereinafter referred to as "high-temperature reaction treatment"). Reaction result was measured after decreasing the reaction bath temperature to 310° C.

TABLE 1

Result of methacrolein oxidation reaction

|  |  | methacrolein conversion rate % | methacrylic acid selectivity % | methacrylic acid yield |
|---|---|---|---|---|
| Example 1 | early phase of the reaction | 87.26 | 81.19 | 70.85 |
|  | after high-temperature reaction treatment | 89.69 | 83.50 | 74.89 |

As shown, if antimony is added at the ratio of 0.05-0.3 to 10 equivalence of molybdenum, catalysts have strong activity and exhibit excellent activity and selectivity when used under large space velocity. They also exhibit excellent activity and selectivity when used under the condition of small reaction tube diameter and large linear velocity. They can advantageously be used when space velocity is increased for increased production or cost reduction by decreased amount of catalysts is desired.

Example 2

Coated catalyst (catalyst according to the invention) was prepared in the same way as in Example 1 except that 320 g of complex oxide, 16.1 g of antimony trioxide and 45 of strength enhancing material (ceramic fiber) were uniformly mixed. Active component composition of the catalyst obtained was $Mo_{10}V_{0.8}P_{1.15}Cu_{0.4}Cs_{0.5}(NH_4)_{2.1}Sb_{0.7}$.

Methacrolein oxidation reaction was performed as in Example 1 except that this coated catalyst was used. The result is shown in Table 2.

TABLE 2

Result of methacrolein oxidation reaction

|  |  | methacrolein conversion rate % | methacrylic acid selectivity % | methacrylic acid yield |
|---|---|---|---|---|
| Example 2 | early phase of the reaction | 73.31 | 83.91 | 61.51 |
|  | after high-temperature reaction treatment | 81.39 | 85.48 | 69.57 |

Example 3

Coated catalyst (catalyst according to the invention) was prepared in the same way as in Example 1 except that 320 g of complex oxide, 22.7 g of antimony trioxide and 45 g of strength enhancing material (ceramic fiber) were uniformly mixed. Active agent composition of the catalyst obtained was $Mo_{10}V_{0.8}P_{1.55}Cu_{0.4}Cs_{0.5}(NH_4)_{2.1}Sb_{1.0}$. Methacrolein oxidation reaction was performed as in Example 1 except that this coated catalyst was used. The result is shown in Table 3.

TABLE 3

Result of methacrolein oxidation reaction

| | | methacrolein conversion rate % | methacrylic acid selectivity % | methacrylic acid yield |
|---|---|---|---|---|
| Example 3 | early phase of the reaction | 77.88 | 83.98 | 65.40 |
| | after high-temperature reaction treatment | 78.00 | 85.49 | 66.68 |

As shown in Tables 2 and 3, when antimony is added at the ratio of 0.3-1.5 to 10 equivalence of molybdenum, catalysts show great versatility and give excellent performance under industrial conditions.

Example 4

Coated catalyst (catalyst according to the invention) was prepared in the same way as in Example 1 except that 320 g of complex oxide, 40.9 g of antimony trioxide and 45 g of strength enhancing material (ceramic fiber) were uniformly mixed. Active agent composition of the catalyst obtained was $MO_{10}V_{0.8}P_{1.15}Cu_{0.4}Cs_{0.5}(NH_4)_{2.1}Sb_{1.8}$. Methacrolein oxidation reaction was performed as in Example 1 except that this coated catalyst was used. The result is shown in Table 4.

TABLE 4

Result of methacrolein oxidation reaction

| | | methacrolein conversion rate % | methacrylic acid selectivity % | methacrylic acid yield |
|---|---|---|---|---|
| Example 4 | early phase of the reaction | 66.45 | 85.92 | 57.09 |
| | after high-temperature reaction treatment | 57.99 | 88.18 | 51.14 |

As shown, when antimony is added at the ratio of 1.5-2.0 to 10 equiv of molybdenum, catalysts show higher selectivity as compared with the catalysts described in Examples 1-3 when used under conditions with smaller space velocity.

Examples 1-4 demonstrate that easy control of catalytic activity and preparation of catalysts having versatility in many reaction conditions can be achieved by adding antimony.

Example 5

Complex oxide was obtained in the same way as in Example 1 except that 916.4 g of an aqueous solution containing 9.1% by mass of cesium hydroxide and 1497.9 g of an aqueous solution containing 14.3% by mass of ammonium acetate were used. 320 g of the complex oxide, 22.7 g of antimony trioxide and 45 g of strength enhancing material (ceramic fiber) were uniformly mixed and coat molded to 300 g of spherical porous alumina carriers (particle diameter 3.5 mm) using 90% by mass of ethanol aqueous solution as a binder. Resultant molding was then calcined for five hours at 380° C. under flowing air to give a desired coated catalyst (catalyst according to the invention).

Composition of the catalyst obtained was $Mo_{10}V_{0.8}P_{1.15}Cu_{0.4}Cs_{1.0}(NH_4)_{5.0}Sb_{1.0}$. Methacrolein oxidation reaction was performed as in Example 1 except that this coated catalyst was used. The result is shown in Table 5.

TABLE 5

Result of methacrolein oxidation reaction

| | | methacrolein conversion rate % | methacrylic acid selectivity % | methacrylic acid yield |
|---|---|---|---|---|
| Example 5 | early phase of the reaction | 77.97 | 82.79 | 64.55 |
| | after high-temperature reaction treatment | 72.19 | 84.91 | 61.30 |

Example 6

To 5680 ml of water were added to 800 g of molybdic anhydride, 40.43 g of vanadium pentoxide and 73.67 g of 85% by mass orthophosphate, stirred for three hours at 92° C. to yield rust-colored clear solution. The solution was then cooled to 15-20° C. To the cooled solution, 458.2 g of an aqueous solution containing 9.1% by mass of cesium hydroxide and 629.1 g of an aqueous solution containing 14.3% by mass of ammonium acetate were gradually added at the same time, and maturation for one hour at 15-20° C. provided yellow slurry.

To the slurry, 709.9 g of an aqueous solution containing 6.3% by mass cupric acetate was added, and additional maturation was performed for 30 minutes at 15-20° C. 32.4 g of antimony trioxide was added to the slurry and maturation was continued for additional 30 minutes at 15-20° C. The slurry was the spray dried to yield dry powder. Composition of the complex powder obtained was $Mo_{10}V_{0.8}P_{1.15}Cu_{0.4}Cs_{0.5}(NH_4)_{2.1}Sb_{0.4}$.

320 g of the dry powder and 45 g of strength enhancing material (ceramic fiber) were then uniformly mixed and coat molded to 300 g of spherical porous alumina carriers (particle diameter 3.5 mm) using approximately 80 g of 90% by mass ethanol aqueous solution as a binder. Resultant molding was calcined for five hours at 380° C. under flowing air to give a desired coated catalyst (catalyst according to the invention). Methacrolein oxidation reaction was performed as in Example 1 except that this coated catalyst was used. The result is shown in Table 6.

TABLE 6

Result of methacrolein oxidation reaction

| | | methacrolein conversion rate % | methacrylic acid selectivity % | methacrylic acid yield |
|---|---|---|---|---|
| Example 6 | early phase of the reaction | 72.79 | 83.63 | 60.87 |
| | after high-temperature reaction treatment | 82.22 | 86.11 | 70.80 |

Example 7

The coated catalyst of Example 3 was filled in a steel reaction tube with internal diameter of 29.4 mm that was equipped with a thermo couple protection tube with external diameter of 6 mm so that height of filled layer 350 cm has been achieved, and isobutylene was supplied to the reaction tube so that the space velocity of 800 h$^{-1}$ of the reacted gas was achieved when reacted with molecular oxygen in the presence of a complex oxide catalyst (molybdenum, bismuth, cobalt and iron are major constituents).

Composition of the reacted gas was 3.21 vol % methacrolein, 8.99 vol % oxygen, 71.54 vol % nitrogen, 14.46 vol % water vapor and 1.80 vol % remaining components.

The result of methacrolein oxidation reaction 2000 hours after the start of the reaction is shown in Table 7.

TABLE 7

Result of methacrolein oxidation reaction

| | reaction bath temperature/° C. | hot spot temperature/° C. | methacrolein conversion rate % | methacrylic acid selectivity % |
|---|---|---|---|---|
| Example 7 | 294 | 315 | 72.79 | 83.63 |

Example 8

41.2 mL of the coated catalysts obtained in Examples 1, 3 and 4 were filled in a stainless reaction tube with an internal diameter of 18.4 mm. A raw material gas (composition (molar ratio); methacrolein:oxygen:water vapor:nitrogen=1:2:4:18.6) was flowed into the reaction tube at 300 hr$^{-1}$ of space velocity (SV), and methacrolein conversion rate, methacrylic acid selectivity and methacrylic acid yield were determined 24 hours after beginning of the reaction.

The result is shown in Table 8.

TABLE 8

Result of methacrolein oxidation reaction

| | antimony amount | reaction bath temperature/° C. | methacrolein conversion rate % | methacrylic acid selectivity % | methacrylic acid yield % |
|---|---|---|---|---|---|
| Example 1 | 0.3 | 265 | 74.26 | 77.23 | 57.35 |
| Example 3 | 1.0 | 270 | 79.71 | 79.89 | 63.68 |
| Example 4 | 1.8 | 275 | 78.40 | 80.46 | 63.08 |

Comparative Example 1

To 5680 ml of water were added to 800 g of molybdic anhydride, 40.43 g of vanadium pentoxide and 73.67 g of 85% by mass orthophosphate, stirred for three hours at 92° C. to yield rust-colored clear solution. Subsequently, 32.4 g of antimony trioxide was added to the solution and heated with stirring for additional two hours at 92° C. to give navy blue solution.

The solution was then cooled to 15-20° C. and 458.2 g of an aqueous solution containing 9.1% by mass of cesium hydroxide and 629.1 g of an aqueous solution containing 14.3% by mass of ammonium acetate were gradually added thereto at the same time with stirring, and one hour of maturation at 15-20° C. provided slurry.

To the slurry, 709.9 g of 6.3% by mass cupric acetate aqueous solution was then gradually added, and maturation was continued for additional 30 minutes at 15-20° C.

The slurry was then spray dried to provide complex oxide powder. The composition of the powder produced is $MO_{10}V_{0.8}P_{1.15}Cu_{0.4}Cs_{0.5}(NH_4)_{2.1}Sb_{0.4}$.

320 g of the complex oxide powder and 45 g of strength enhancing material (ceramic fiber) were uniformly mixed and coat molded to 300 g of spherical porous alumina carriers (particle diameter 3.5 mm) using approximately 80 g of 90% by mass ethanol aqueous solution as a binder. Resultant molding was then calcined for five hours at 380° C. under flowing air to give a coated catalyst for comparison. Methacrolein oxidation reaction was performed as in Example 1 except that this coated catalyst was used, but methacrolein conversion rate was as low as 15% and could not be used as a practical catalyst.

The invention claimed is:

1. A method for manufacturing a catalyst comprising essential active components of molybdenum, phosphorus, vanadium, cesium, antimony, and ammonia for use in the production of methacrylic acid, comprising mixing an antimony compound selected from the group consisting of antimony trioxide, antimony pentoxide and antimony acetate, with a complex oxide containing the essential active components other than antimony, and molding and calcining the resulting mixture.

2. The method according to claim 1, wherein the mixing of the antimony compound with the complex oxide is a mechanical mixing of the complex oxide and a solid antimony compound.

3. A method for manufacturing a catalyst comprising essential active components of molybdenum, phosphorus, vanadium, cesium, antimony, and ammonia for use in the production of methacrylic acid, comprising mixing a slurry containing the essential active components other than antimony and being convertible into a complex oxide by heating with an antimony compound selected from the group consisting of antimony trioxide, antimony pentoxide and antimony acetate, wherein the temperature at which the antimony compound is mixed is 0° C. to 35° C., drying the resulting mixture to form a dry powder, and molding and calcining the dry powder.

4. The method according to claim 1 or 2, wherein the molding comprises coating an inactive carrier with the mixture using a binder to form a coated catalyst.

5. The method according to claim 3, wherein the molding comprises coating an inactive carrier with the dry powder using a binder to form a coated catalyst.

6. The method according to claim 4, wherein the binder is water and/or at least one type of liquid selected from the group consisting of an organic compound having a boiling point of 150° C. or less at 1 atmospheric pressure.

7. The method according to claim 1, wherein the calcination temperature is 300° C. to 450° C.

8. A catalyst prepared by the method according to claim 1.

9. A method for producing methacrylic acid, comprising gas-phase catalytic oxidation of methacrolein, isobutyraldehyde, or isobutyric acid using a catalyst according to claim 8.

10. The method according to claim 5, wherein the binder is water and/or at least one type of liquid selected from the group consisting of an organic compound having a boiling point of 150° C. or less at 1 atmosphere pressure.

11. The method according to claim 3, wherein the calcinations temperature is 300° C. to 450° C.

12. A catalyst prepared by the method according to claim 3.

13. A method for producing methacrylic acid, comprising gas-phase catalytic oxidation of methacrolein, isobutyraldehyde, or isobutyric acid using a catalyst according to claim 12.

* * * * *